(12) United States Patent
Hosokawa et al.

(10) Patent No.: US 12,410,150 B2
(45) Date of Patent: Sep. 9, 2025

(54) FLUOROLACTONE AND METHOD FOR PRODUCING SAME

(71) Applicant: DAIKIN INDUSTRIES, LTD., Osaka (JP)

(72) Inventors: Moe Hosokawa, Osaka (JP); Koutarou Hayashi, Osaka (JP); Yoshihiro Yamamoto, Osaka (JP); Akiyoshi Yamauchi, Osaka (JP); Yosuke Kishikawa, Osaka (JP); Yuuki Suzuki, Osaka (JP); Akitoshi Ogata, Osaka (JP); Makoto Matsuura, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 17/398,257

(22) Filed: Aug. 10, 2021

(65) Prior Publication Data

US 2021/0371392 A1    Dec. 2, 2021

Related U.S. Application Data

(63) Continuation of application No. PCT/JP2020/005417, filed on Feb. 12, 2020.

(30) Foreign Application Priority Data

Feb. 12, 2019    (JP) ................. 2019-022993

(51) Int. Cl.
*C07D 319/12* (2006.01)
*C07D 317/42* (2006.01)

(52) U.S. Cl.
CPC ......... *C07D 319/12* (2013.01); *C07D 317/42* (2013.01)

(58) Field of Classification Search
CPC .................................................. C07D 319/12
See application file for complete search history.

(56) References Cited

U.S. PATENT DOCUMENTS

| | | | |
|---|---|---|---|
| 3,308,107 | A | 3/1967 | Selman et al. |
| 3,450,716 | A | 6/1969 | Selman et al. |
| 4,013,689 | A | 3/1977 | Martini |
| 4,035,388 | A | 7/1977 | Martini |
| 4,052,277 | A | 10/1977 | Martini |

(Continued)

FOREIGN PATENT DOCUMENTS

| | | |
|---|---|---|
| JP | 51-136686 | 11/1976 |
| JP | 51-138617 | 11/1976 |

(Continued)

OTHER PUBLICATIONS

"Find ETDs Home > Thesis Resources > Find ETDs" Online: "https://ndltd.org/thesis-resources/find-etds/" Accessed Jan. 31, 2023.*

(Continued)

*Primary Examiner* — David K O'Dell
(74) *Attorney, Agent, or Firm* — Wenderoth, Lind & Ponack, L.L.P.

(57) ABSTRACT

The present disclosure provides, for example, a method that can produce a fluorolactone compound from hexafluoropropylene oxide or the like in a single step. The present disclosure relates to a method for producing a compound represented by formula (1):

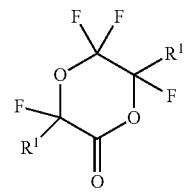

(1)

wherein two $R^1$ are the same and each is a fluorine atom or a fluoroalkyl group,
the method comprising step A of reacting a compound represented by formula (2):

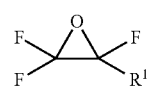

(2)

wherein $R^1$ is as defined above, with a compound (3) represented by formula (3-1) or the like:

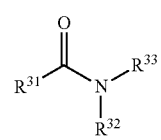

(3-1)

wherein $R^{31}$, $R^{32}$, and $R^{33}$ are the same or different and each is a hydrogen atom or a $C_{1-10}$ alkyl group, or two of them are optionally linked to each other to form a ring optionally having one or more substituents,
in the presence of a fluorine compound (4) represented by formula (4-1) or the like:

$$MH_nF_m$$ (4-1)

wherein M is a metal atom, n is 0 or 1, and the sum of the valence number of M and n is m, and
an organic solvent, provided that the compound represented by formula (3) is excluded from the organic solvent.

2 Claims, No Drawings

(56) References Cited

U.S. PATENT DOCUMENTS

| | | |
|---|---|---|
| 4,118,398 A | 10/1978 | Martini |
| 4,118,399 A | 10/1978 | Martini |
| 4,140,699 A | 2/1979 | Martini |
| 6,118,026 A * | 9/2000 | Mitsui .................. C07F 5/027 568/1 |

FOREIGN PATENT DOCUMENTS

| | | |
|---|---|---|
| JP | 52-10209 | 1/1977 |
| JP | 52-142078 | 11/1977 |
| JP | 2005-2014 | 1/2004 |
| JP | 2005002014 A * | 1/2005 |

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*

Liu "Free-radical polymerization of dioxolane and dioxane derivatives: Effect of fluorine substituents on the ring opening polymerization" Journal of Polymer Science: Part A: Polymer Chemistry, vol. 42, 5180-5188 (2004).*

Sullivan, Raymond "Synthesis of Perfluoroalkyl Vinyl Ether Acids and Derivatives" Journal of Organic Chemistry 1969 34, 6, 1841-44.*

P. Jusforgues, "Large-Scale Gas Chromatography" in the Encyclopedia of Separation Science, 2000 Academic Press pp. 529-536.*

International Search Report issued Mar. 24, 2020 in International (PCT) Application No. PCT/JP2020/005417.

Mikes et al., "Synthesis and Characterization of an Amorphous Perfluoropolymer: Poly(perfluoro-2-methylene-4-methyl-1,3-dioxolane)", Macromolecules, 2005, vol. 38, No. 10, pp. 4237-4245.

The Fifth Series of Experimental Chemistry 16 Organic Compound Compositions IV, carboxylic acid, amino acids, peptides, 2007, p. 10, with partial English translation.

Yuminov et al., "Synthesis of Dome Derivatives of Perfluoro-4-Oxo-1,2-Dioxolane", Bulletin of the Academy of Sciences of the USSR, 1988, vol. 37, No. 2, pp. 311-315.

Millauer et al., "Hexafluoropropene Oxide—A Key Compound in Organofluorine Chemistry", Angew. Chem. International Edition in English, 1985, vol. 24, pp. 161-179.

Partial Supplementary European Search Report issued Aug. 1, 2022 in corresponding European Patent Application No. 20755235.7.

Extended European Search Report dated Nov. 11, 2022 in European Patent Application No. 20755235.7.

International Preliminary Report on Patentability issued Aug. 10, 2021 in corresponding International Patent Application No. PCT/JP2020/005417.

Partial European Search Report issued Sep. 3, 2024, in corresponding European Patent Application No. 24180164.6, pp. 1-15.

Extended European Search Report issued Nov. 26, 2024 in corresponding European Patent Application No. 24180164.6.

M. Hudlicky, "Chemistry of Organic Fluorine Compounds", Shanghai Science and Technology Press (1965), pp. 195-198, with English translation.

* cited by examiner

FLUOROLACTONE AND METHOD FOR PRODUCING SAME

TECHNICAL FIELD

The present disclosure relates to fluorolactone, a method for producing the same, and the like.

BACKGROUND ART 2-(Difluoromethylene)-4,4,5-trifluoro-5-(trifluoromethyl)-1,3-dioxolane is used as a fluororesin raw material. As a method for producing perfluorodioxolane, a method using 3,5,5,6-tetrafluoro-3,6-bis(trifluoromethyl)-1,4-dioxane-2-one as a raw material is known, as shown in the following formula (e.g., PTL 1).

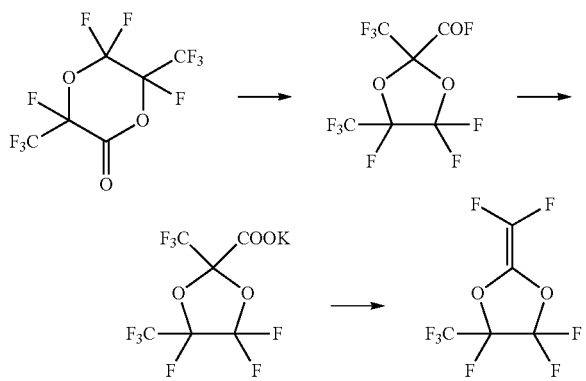

Further, as a method for producing perfluorodioxane, for example, a two-step method using hexafluoropropylene oxide as a raw material is known, as shown in the following formula (e.g., NPL 1).

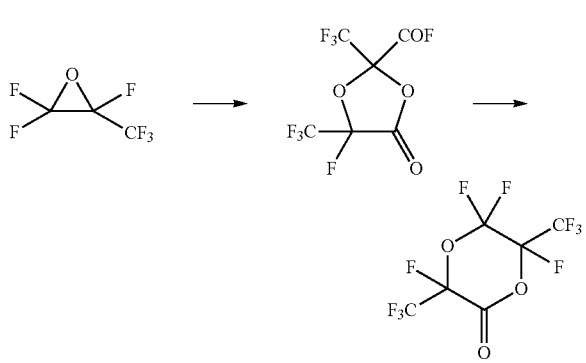

CITATION LIST

Patent Literature

PTL 1: JP2005-2014A

Non-Patent Literature

NPL 1: "Perfluorinated dioxolanes 1. Synthesis of some derivatives of perfluoro-4-oxo-1,3-dioxolane," V. S. Yuminov, S. V. Kartsov, V. L. Maksimov, and A. V. Fokin, Bulletin of the Academy of Sciences of the USSR, 1988, 37(2), 311-315.

SUMMARY

The present disclosure includes, for example, the following embodiment.

A method for producing a compound represented by formula (1):

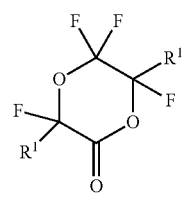

(1)

wherein two $R^1$ are the same and each is a fluorine atom or a fluoroalkyl group, the method comprising step A of reacting a compound represented by formula (2):

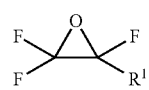

(2)

wherein $R^1$ is as defined above, with at least one compound (3) selected from the group consisting of:

a compound represented by formula (3-1):

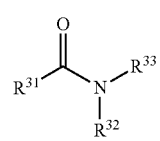

(3-1)

wherein $R^{31}$, $R^{32}$, and $R^{33}$ are the same or different and each is a hydrogen atom or a $C_{1-10}$ alkyl group, or two of them are optionally linked to each other to form a ring optionally having one or more substituents; and a compound represented by formula (3-2):

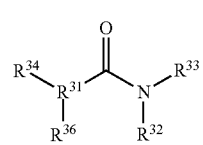

(3-2)

wherein $R^{34}$, $R^{35}$, $R^{36}$, and $R^{37}$ are the same or different and each is a hydrogen atom or a $C_{1-10}$ alkyl group, or two of them are optionally linked to each other to form a ring optionally having one or more substituents, in the presence of at least one fluorine compound (4) selected from the group consisting of:

a compound represented by formula (4-1):

$$MH_nF_m \quad (4\text{-}1)$$

wherein M is a metal atom, n is 0 or 1, and the sum of the valence number of M and n is m;

a compound represented by formula (4-2):

$$LR^{41}{}_4F \quad (4\text{-}2)$$

wherein L is a nitrogen atom or a phosphorus atom, and $R^{41}$ are the same or different and each is a $C_{1\text{-}5}$ alkyl group; and hydrofluoric acid or a salt thereof, and an organic solvent, provided that the compounds represented by formulas (3-1) and (3-2) are excluded from the organic solvent.

Advantageous Effects

The present disclosure provides, for example, a method that can produce a fluorolactone compound from hexafluoropropylene oxide or the like in a single step. The present disclosure provides a novel fluorodioxolane compound, a method for producing the same, and the like.

DESCRIPTION OF EMBODIMENTS

The above summary of the present disclosure is not intended to describe each disclosed embodiment or every implementation of the present disclosure.

The following description of the present disclosure illustrates embodiments of examples in more detail.

In several parts of the present disclosure, guidance is provided through examples, and these examples can be used in various combinations.

In each case, the group of examples can act as a non-exclusive and representative group.

All publications, patents, and patent applications referred to herein are incorporated herein by reference without modification.

Terms

Unless otherwise specified, the symbols and abbreviations in the present specification can be understood in the sense commonly used in the technical field to which the present disclosure pertains, according to the context of the present specification.

In the present specification, the terms "contain" and "comprise" are used with the intention to include the terms "consist essentially of" and "consist of."

Unless otherwise specified, the steps, treatments, or operations described in the present specification can be performed at room temperature.

In the present specification, room temperature can mean a temperature in the range of 10 to 40° C.

In the present specification, the notation "Cn," (where n and m are numbers) indicates that the number of carbon atoms is n or more and m or less, as is commonly understood by a person skilled in the art.

In the present specification, unless otherwise specified, examples of the "substituent" include halogen atoms, alkyl groups, cyano groups, amino groups, alkoxy groups, and alkylthio groups. The number of substituents can be within the range from one to the maximum substitutable number (e.g., 1, 2, 3, 4, 5, or 6), preferably 1 to 4, more preferably 1 to 3, and particularly preferably 1 or 2. Two or more substituents may be the same or different.

In the present specification, unless otherwise specified, the "organic group" refers to a group formed by removing one hydrogen atom from an organic compound. As can be understood from this, organic groups have one or more carbon atoms.

In the present specification, unless otherwise specified, the "organic group" includes:
(1) a hydrocarbon group, and
(2) a hydrocarbon group having one or more heteroatoms (e.g., nitrogen, oxygen, sulfur, phosphorus, and halogen).

In the present specification, unless otherwise specified, the "hydrocarbon group" refers to a group consisting of carbon and hydrogen. Hydrocarbon groups are also called "hydrocarbyl groups."

In the present specification, unless otherwise specified, examples of the "hydrocarbon group" include:
(1) aliphatic hydrocarbon groups optionally substituted with one or more aromatic hydrocarbon groups (e.g., benzyl groups); and
(2) aromatic hydrocarbon groups optionally substituted with one or more aliphatic hydrocarbon groups.

Aromatic hydrocarbon groups are also called "aryl groups."

In the present specification, unless otherwise specified, the "aliphatic hydrocarbon group" can have a linear, branched, or cyclic structure, or a combination thereof.

In the present specification, unless otherwise specified, the "aliphatic hydrocarbon group" can be saturated or unsaturated.

In the present specification, unless otherwise specified, examples of the "aliphatic hydrocarbon group" include alkyl groups, alkenyl groups, alkynyl groups, and cycloalkyl groups.

In the present specification, unless otherwise specified, examples of the "alkyl group" include linear or branched $C_{1\text{-}10}$ alkyl groups, such as methyl, ethyl, propyl (e.g., n-propyl and isopropyl), butyl (e.g., n-butyl, isobutyl, sec-butyl, and tert-butyl), pentyl (e.g., n-pentyl, tert-pentyl, neopentyl, isopentyl, sec-pentyl, and 3-pentyl), hexyl, heptyl, octyl, nonyl, and decyl.

In the present specification, unless otherwise specified, examples of the "alkenyl group" include linear or branched $C_{1\text{-}10}$ alkenyl groups. Specific examples include vinyl, 1-propenyl, isopropenyl, 2-methyl-1-propenyl, 1-butenyl, 2-butenyl, 3-butenyl, 2-ethyl-1-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, and 5-hexenyl.

In the present specification, unless otherwise specified, examples of the "alkynyl group" include linear or branched $C_{2\text{-}6}$ alkynyl groups. Specific examples include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

In the present specification, unless otherwise specified, examples of the "cycloalkyl group" include $C_{3\text{-}10}$ cycloalkyl groups. Specific examples include cyclopropyl, cyclobutyl, cyclopentyl, cyclohexyl, cycloheptyl, cyclooctyl, and adamantyl.

In the present specification, unless otherwise specified, examples of the "aromatic hydrocarbon group (aryl group)" include $C_{6\text{-}14}$ aromatic hydrocarbon groups (aryl groups). Specific examples include phenyl, naphthyl, phenanthryl, anthryl, and pyrenyl.

In the present specification, unless otherwise specified, examples of the "aromatic hydrocarbon ring" include $C_{6\text{-}14}$ aromatic hydrocarbon rings. Specific examples include benzene, naphthalene, anthracene, and phenanthrene rings.

In the present specification, unless otherwise specified, the "fluoroalkyl group" refers to a group formed by replacing one or more hydrogen atoms of an alkyl group with a fluorine atom, and also includes a perfluoroalkyl group formed by replacing all the hydrogen atoms of an alkyl group. Examples of the "fluoroalkyl group" include linear or branched $C_{1-10}$ fluoroalkyl groups, such as mono-, di-, or trifluoromethyl, mono-, di-, tri-, tetra-, or hexafluoroethyl, mono-, di-, tri-, tetra-, hexa-, or heptafluorobutyl, mono-, di-, tri-, tetra-, hexa-, hepta-, octa-, or nonafluorobutyl, and mono-, di-, tri-, tetra-, hexa-, hepta-, octa-, nona-, deca-, or undecafluoropentyl.

Methods for Producing Compound Represented by Formula (1)

An embodiment of the present disclosure is a method for producing a compound represented by formula (1):

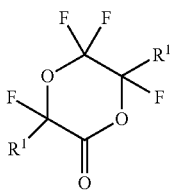

(1)

wherein two $R^1$ are the same and each is a fluorine atom or a fluoroalkyl group (in the present specification, also referred to as "compound (1)").

This method comprises step A of reacting a compound represented by formula (2):

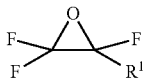

(2)

wherein $R^1$ is as defined above (in the present specification, also referred to as "compound (2)"), with at least one compound (3) (in the present specification, also referred to as "compound (3)") selected from the group consisting of:

a compound represented by formula (3-1):

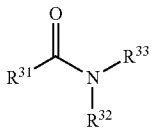

(3-1)

wherein $R^{31}$, $R^{32}$, and $R^{33}$ are the same or different and each is a hydrogen atom or a $C_{1-10}$ alkyl group, or two of them are optionally linked to each other to form a ring optionally having one or more substituents (in the present specification, also referred to as "compound (3-1)"); and a compound represented by formula (3-2):

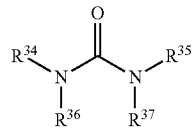

(3-2)

wherein $R^{34}$, $R^{35}$, $R^{36}$, and $R^{37}$ are the same or different and each is a hydrogen atom or a $C_{1-10}$ alkyl group, or two of them are optionally linked to each other to form a ring optionally having one or more substituents (in the present specification, also referred to as "compound (3-2)"), in the presence of at least one fluorine compound (4) (in the present specification, also referred to as "compound (4)") selected from the group consisting of:

a compound represented by formula (4-1):

$$MH_nF_m \quad (4\text{-}1)$$

wherein M is a metal atom, n is 0 or 1, and the sum of the valence number of M and n is m (in the present specification, also referred to as "compound (4-1)");

a compound represented by formula (4-2):

$$LR^{41}_4F \quad (4\text{-}2)$$

wherein L is a nitrogen atom or a phosphorus atom, and $R^{41}$ are the same or different and each is a $C_{1-5}$ alkyl group (in the present specification, also referred to as "compound (4-2)"); and hydrofluoric acid or a salt thereof, and an organic solvent, provided that the compounds represented by formulas (3-1) and (3-2) are excluded from the organic solvent.

$R^1$ is preferably a fluorine atom or a $C_{1-10}$ fluoroalkyl group, more preferably a fluorine atom or a $C_{1-5}$ perfluoroalkyl group, even more preferably a fluorine atom or a $C_{1-3}$ perfluoroalkyl group, and particularly preferably a $C_{1-3}$ perfluoroalkyl group.

Preferred specific examples of compound (2) include hexafluoropropylene oxide, 2,2,3-trifluoro-3-(perfluoroethyl)oxirane, and 2,2,3-trifluoro-3-(perfluoropropyl)oxirane.

Preferably, $R^3$, $R^{32}$, and $R^{33}$ are the same or different and each is a hydrogen atom or a $C_{1-5}$ alkyl group;

$R^{31}$ is a hydrogen atom or a $C_{1-5}$ alkyl group, $R^{32}$ and $R^{33}$ are linked to form a pyrrolidone ring or piperidine ring optionally having one or two substituents on the carbon atoms in the ring, the substituent is methyl or ethyl, and if there are two or more substituents, they may be the same or different; or $R^{31}$ and $R^{32}$ are linked to form a pyrrolidone ring or piperidinone ring optionally having one or two substituents on the carbon atoms in the ring, the substituent is methyl or ethyl, if there are two or more substituents, they may be the same or different, and $R^{33}$ is a hydrogen atom or a $C_{1-5}$ alkyl group.

More preferably, $R^{31}$, $R^{32}$, and $R^{33}$ are the same or different and each is a hydrogen atom or a $C_{1-3}$ alkyl group;

$R^{31}$ is a hydrogen atom or a $C_{1-3}$ alkyl group, and $R^{32}$ and $R^{33}$ are linked to form a pyrrolidone ring or a piperidine ring; or $R^{31}$ and $R^{32}$ are linked to form a pyrrolidone ring or a piperidinone ring, and $R^{33}$ is a hydrogen atom or a $C_{1-3}$ alkyl group.

Even more preferably, $R^{31}$, $R^{32}$, and $R^{33}$ are the same or different and each is a hydrogen atom or a $C_{1-3}$ alkyl group;

$R^{31}$ is a hydrogen atom or a $C_{1-3}$ alkyl group, and $R^{32}$ and $R^{33}$ are linked to form a pyrrolidone ring; or $R^{31}$ and $R^{32}$ are linked to form a pyrrolidone ring, and $R^{33}$ is a $C_{1-3}$ alkyl group.

Particularly preferably, $R^{31}$, $R^{32}$, and $R^{33}$ are the same or different and each is a hydrogen atom, methyl, or ethyl;

$R^{31}$ is a hydrogen atom, methyl, or ethyl, and $R^{32}$ and $R^{33}$ are linked to form a pyrrolidone ring; or $R^{31}$ and $R^{32}$ are linked to form a pyrrolidone ring, and $R^{33}$ is a hydrogen atom, methyl, or ethyl.

Preferred specific examples of compound (3-1) include formic acid amide, N,N-dimethylacetamide, N,N-dimethylformamide, N-methyl-2-pyrrolidone, and N-ethyl-2-pyrrolidone.

Preferably, $R^{34}$, $R^{35}$, $R^{36}$, and $R^{37}$ are the same or different and each is a hydrogen atom or a $C_{1-5}$ alkyl group; or $R^{34}$ and $R^{35}$ are the same or different and each is a hydrogen atom or a $C_{1-5}$ alkyl group, $R^{36}$ and $R^{37}$ are linked to each other to form a tetrahydropyrimidine ring or imidazolidine ring optionally having one or two substituents on the carbon atoms in the ring, and the substituent is methyl or ethyl.

More preferably, $R^{34}$, $R^{35}$, $R^{36}$, and $R^{37}$ are the same or different and each is a hydrogen atom or a $C_{1-3}$ alkyl group; or $R^{34}$ and $R^{35}$ are the same or different and each is a hydrogen atom or a $C_{1-3}$ alkyl group, and $R^{36}$ and $R^{37}$ are linked to each other to form a tetrahydropyrimidine ring or an imidazolidine ring.

Even more preferably, $R^{34}$, $R^{35}$, $R^{36}$, and $R^{37}$ are the same or different and each is a hydrogen atom, methyl, or ethyl; or $R^{34}$ and $R^{35}$ are the same or different and each is a hydrogen atom, methyl, or ethyl, and $R^{36}$ and $R^{37}$ are linked to each other to form a tetrahydropyrimidine ring or an imidazolidine ring.

Particularly preferably, $R^{34}$, $R^{35}$, $R^{36}$, and $R^{37}$ are the same or different and each is methyl or ethyl; or $R^{34}$ and $R^{35}$ are the same and each is methyl or ethyl, and $R^{36}$ and $R^{37}$ are linked to each other to form a tetrahydropyrimidine ring.

Preferred specific examples of compound (3-2) include N,N'-dimethylpropylene urea, N,N'-dimethylethylene urea, and tetramethyl urea.

In an embodiment of the present disclosure, preferred specific examples of compound (3) include at least one compound selected from the group consisting of formic acid amide, N,N-dimethylacetamide, N, N-dimethylformamide, N-methyl-2-pyrrolidone, N-ethyl-2-pyrrolidone, N,N'-dimethylpropylene urea, N,N'-dimethylethylene urea, tetramethyl urea, N,N'-diethylpropylene urea, and N,N'-diethylethylene urea.

M is preferably an alkali metal atom or an alkaline earth metal atom; more preferably an alkali metal atom, a magnesium atom, or a calcium atom; even more preferably an alkali metal atom or a calcium atom; and particularly preferably a sodium atom, a potassium atom, a cesium atom, or a calcium atom.

Preferably, M is an alkali metal atom, and n is 0 or 1; or M is an alkaline earth metal atom, and n is 0.

More preferably, M is a sodium atom, a potassium atom, or a cesium atom, and n is 0 or 1; or M is a calcium atom, and n is 0.

Even more preferably, M is a potassium atom or a cesium atom, and n is 0 or 1; or M is a calcium atom, and n is 0.

Preferred specific examples of compound (4-1) include cesium fluoride, potassium hydrogen fluoride, calcium fluoride, sodium fluoride, potassium fluoride, and sodium hydrogen fluoride.

Preferably, L is a nitrogen atom or a phosphorus atom, and $R^{41}$ are the same or different and each is a $C_{1-4}$ alkyl group.

More preferably, L is a nitrogen atom or a phosphorus atom, and $R^{41}$ are the same and each is a $C_{1-4}$ alkyl group.

Even more preferably, L is a nitrogen atom or a phosphorus atom, and $R^{41}$ are the same and each is a linear $C_{1-4}$ alkyl group.

Particularly preferably, L is a nitrogen atom or a phosphorus atom, and $R^{41}$ are the same and each is methyl, ethyl, or n-butyl.

Preferred specific examples of compound (4-2) include tetrabutylammonium fluoride, tetraethylammonium fluoride, tetramethylammonium fluoride, tetrabutylphosphonium fluoride, and triethylmethylammonium fluoride.

Salts of hydrofluoric acid include amine salts, ammonium salts, imidazolium salts, pyridinium salts, phosphonium salts, and the like. These salts may contain one or more substituents. If there are two or more substituents, they may be the same or different.

The amine salt of hydrofluoric acid is preferably substituted. The number of substituents is, for example, 1 to 3, preferably 2 or 3, and more preferably 3. When there are two or more substituents, they may be the same or different. Preferred substituents are $C_{1-10}$ alkyl groups, more preferably $C_{1-5}$ alkyl groups, and particularly preferably $C_{1-4}$ alkyl groups.

Preferred examples of amine salts of hydrofluoric acid include tri-$C_{1-4}$ alkylamine hydrofluoride (the number of HF– may be any integer of 1 to 7).

Preferred specific examples of amine salts of hydrofluoric acid include trimethylamine hydrofluoride (the number of HF– may be any integer of 1 to 7, and preferably 3, 4, or 5) and triethylamine hydrofluoride (the number of HF– may be any integer of 1 to 7, and preferably 3, 4, or 5).

When the ammonium salt of hydrofluoric acid is substituted, the number of substituents is, for example, 1 to 4, preferably 2 to 4, more preferably 3 or 4, and particularly preferably 4. When there are two or more substituents, they may be the same or different. Preferred substituents are $C_{1-10}$ alkyl groups, more preferably $C_{1-5}$ alkyl groups, and particularly preferably $C_{1-4}$ alkyl groups.

Preferred specific examples of ammonium salts of hydrofluoric acid include ammonium fluoride, ammonium hydrogen fluoride, and tetra-$C_{1-4}$ alkylammonium fluoride.

Preferred specific examples of ammonium salts of hydrofluoric acid include ammonium fluoride, ammonium hydrogen fluoride, tetramethylammonium fluoride, tetraethylammonium fluoride, and tetrabutylammonium fluoride.

The imidazolium salt of hydrofluoric acid is preferably such that the nitrogen atoms in the imidazolium ring are substituted. The number of substituents is, for example, 1 to 3, preferably 2 or 3, and more preferably 2. When there are two or more substituents, they may be the same or different. Preferred substituents are $C_{1-10}$ alkyl groups (e.g., methyl, ethyl, n-propyl, isopropyl, n-butyl, and tert-butyl), cyclohexyl, vinyl, and allyl; and particularly preferably $C_{1-3}$ alkyl groups.

Preferred specific examples of imidazolium salts of hydrofluoric acid include 1-methyl-3-methylimidazolium fluoride and 1-ethyl-3-methylimidazolium fluoride.

The pyridinium salt of hydrofluoric acid may be substituted. The number of substituents is, for example, 1 to 3, and preferably 1 or 2. When there are two or more substituents, they may be the same or different. Preferred substituents are $C_{1-10}$ alkyl groups, more preferably $C_{1-5}$ alkyl groups, and particularly preferably $C_{1-4}$ alkyl groups.

Preferred specific examples of pyridinium salts of hydrofluoric acid include pyridinium poly(hydrogen fluoride) (the number of HF may be any integer of 1 to 9, and preferably 1 or 9).

The phosphonium salt of hydrofluoric acid is preferably substituted. The number of substituents is, for example, 1 to 4, preferably 3 or 4, and more preferably 4. Preferred substituents are $C_{1-10}$ alkyl groups, optionally substituted phenyl, and optionally substituted benzyl; more preferably $C_{1-5}$ alkyl groups; and particularly preferably $C_{1-4}$ alkyl groups.

Preferred specific examples of phosphonium salts of hydrofluoric acid include tetramethylphosphonium hydrofluoride, tetraethylphosphonium hydrofluoride, tetrapropylphosphonium hydrofluoride, tetrabutylphosphonium hydrofluoride, tetraoctylphosphonium hydrofluoride, trimethylethylphosphonium hydrofluoride, triethylmethylphosphonium hydrofluoride, hexyltrimethylphosphonium hydrofluoride, trimethyloctylphosphonium hydrofluoride, triethyl(methoxymethyl)phosphonium hydrofluoride, and triethyl(methoxymethyl)phosphonium hydrofluoride.

In an embodiment of the present disclosure, preferred specific examples of compound (4) include at least one fluorine compound selected from the group consisting of cesium fluoride, potassium hydrogen fluoride, calcium fluoride, sodium fluoride, potassium fluoride, sodium hydrogen fluoride, tetrabutylammonium fluoride, tetraethylammonium fluoride, tetramethylaimmonium fluoride, tetrabutylphosphonium fluoride, triethylmethylammonium fluoride, triethylamine trihydrofluoride, triethylamine pentahydrofluoride, triethylamine heptahydrofluoride, pyridinium poly(hydrogenfluoride), pyridine monohydrofluoride, pyridinium poly(hydrogenfluoride), pyridine nonahydrofluoride, ammonium hydrogen fluoride, and ammonium fluoride.

Examples of organic solvents include aromatic solvents, ester solvents, ketone solvents, saturated hydrocarbon solvents, nitrile solvents, ether solvents, sulfoxide solvents, and halogenated hydrocarbon solvents. These organic solvents can be used singly or in combination of two or more.

Preferred examples of organic solvents include ether solvents, ester solvents, halogenated hydrocarbon solvents, and nitrile solvents.

Preferred specific examples of aromatic solvents include benzene, toluene, and xylene.

Preferred specific examples of ester solvents include methyl formate, ethyl formate, methyl acetate, ethyl acetate, isopropyl acetate, methyl propionate, ethyl propionate, and n-butyl acetate.

Preferred specific examples of ketone solvents include acetone, methyl ethyl ketone, methyl isobutyl ketone, and cyclohexanone.

Preferred specific examples of saturated hydrocarbon solvents include n-pentane, n-hexane, cyclohexane, and n-heptane.

Preferred specific examples of nitrile solvents include 1,4-dicyanobutane, acetonitrile, and benzonitrile.

Preferred specific examples of ether solvents include diethylene glycol dimethyl ether, triethylene glycol dimethyl ether, tetraethylene glycol dimethyl ether, diethyl ether, diisopropyl ether, dioxane, tetrahydrofuran, 1,2-dimethoxyethane, and crown ether.

Preferred specific examples of sulfoxide solvents include dimethyl sulfoxide and sulfolane.

Preferred specific examples of halogenated hydrocarbon solvents include methylene chloride, chloroform, carbon tetrachloride, 1,2-dichloroethane, 1,2-dichlorobenzene, and chlorobenzene.

Preferred specific examples of organic solvents include ethyl acetate, diethylene glycol dimethyl ether, triethylene glycol dimethyl ether, tetraethylene glycol dimethyl ether, 1,4-dicyanobutane, methylene chloride, chloroform, tetrahydrofuran, and acetonitrile.

In the present disclosure, compounds (3-1) and (3-2) are considered to act as reactants in step A. Compounds (3-1) and (3-2) are excluded from the organic solvent in step A.

Step A

The amount of compound (3) used in step A may be preferably within the range of 0.05 to 10 mol, more preferably 0.08 to 5 mol, and even more preferably 0.1 to 2 mol, per mol of compound (2).

The amount of compound (4) used in step A may be preferably within the range of 0.001 to 0.3 mol, more preferably 0.002 to 0.1 mol, and even more preferably 0.006 to 0.1 mol, per mol of compound (2).

The amount of the organic solvent used in step A may be an amount that can function as a solvent, based on common technical knowledge etc. The amount of the organic solvent used in step A may be preferably within the range of 0.1 to 50 mol, more preferably 0.1 to 20 mol, and even more preferably 0.1 to 10 mol, per mol of compound (2).

The reaction temperature in step A may be preferably within the range of −30 to 40° C., more preferably −30 to 30° C., and even more preferably −20 to 30° C. As the reaction temperature in step A decreases, the selectivity of compound (1) tends to increase. As the reaction temperature in step A increases, the reactivity tends to increase.

The reaction time in step A may be preferably within the range of 0.5 hours to 48 hours, more preferably 0.5 hours to 24 hours, and even more preferably 0.5 hours to 12 hours.

The reaction in step A may be performed in the presence or absence of an inert gas (e.g., nitrogen gas), and preferably in the absence of an inert gas.

Step A can be performed under reduced pressure, atmospheric pressure, or increased pressure.

In step A, compounds (2) and (3) may be reacted in an organic solvent. Step A is preferably performed by mixing compound (3), compound (4), and an organic solvent, cooling the mixture (e.g., −30° C.), and adding compound (2) thereto.

Compound (1) produced in step A can be isolated or purified, if desired, by a conventional method, such as extraction, dissolution, concentration, precipitation, dehydration, adsorption, distillation, rectification, or chromatography, or a combination of these methods.

In a conventional method for producing compound (1) by reacting hexafluoropropylene oxide with N,N-dimethylformamide at 0° C. (first reaction), and then heating the reactant at 140° C. in diethylene glycol dimethyl ether in the presence of cesium fluoride (second reaction), a large amount of difluoroamine is produced as a by-product during the first reaction. Since difluoroamine converts the target compound (1) into another compound, it is necessary to trap and remove difluoroamine with HCl gas, which is harmful to human health, before the second reaction. In step A of the present disclosure, the use of a solvent eliminates the need to trap difluoroamine with HCl gas, because difluoroamine is transferred to the solvent and the contact between difluoroamine and compound (1) is suppressed.

In the method disclosed in PTL 1, fluorine gas, which is difficult to handle and dangerous, is used in the production of 3,5,5,6-tetrafluoro-3,6-bis(trifluoromethyl)-1,4-dioxane-2-one. Further, in the method disclosed in PTL 1, 3,5,5,6-tetrafluoro-3,6-bis(trifluoromethyl)-1,4-dioxane-2-one is produced as a mixture and is difficult to purify. In contrast, step A of the present disclosure does not require the use of fluorine gas, and the product liquid obtained in step A is easy to purify, and can be purified by liquid separation, for example.

Step B

The method for producing the compound represented by formula (1) of the present disclosure may further comprise step B of performing liquid separation, in addition to step A. The reaction liquid produced in step A can be composed of two layers, an upper liquid layer and a lower liquid layer, one of which contains compound (1). Therefore, the liquid layer containing the target compound (1) can be easily obtained by separating the reaction liquid.

The method for isolating compound (1) from the liquid layer may be a conventional method, such as extraction, dissolution, concentration, precipitation, dehydration, adsorption, distillation, rectification, or chromatography, or a combination of these methods. Since the liquid layer containing compound (1) obtained in step B contains few foreign compounds with a boiling point close to that of compound (1), compound (1) can be easily obtained by distilling the liquid layer.

Methods for Producing Compound Represented by Formula (5)

An embodiment of the present disclosure is a method for producing a compound represented by formula (5):

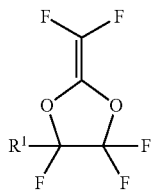

(5)

wherein $R^1$ is a fluorine atom or a fluoroalkyl group (in the present specification, also referred to as "compound (5)").

This method comprises:

step C of heating the compound represented by formula (1) produced in step A or B in the presence of compound (4) to produce a compound represented by formula (6):

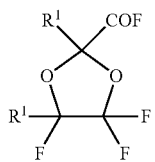

(6)

wherein $R^1$ are as defined above (in the present specification, also referred to as "compound (6)");

step D of reacting the compound represented by formula (6) with a base (in the present specification, also referred to as "base (d)") to produce a compound represented by formula (8):

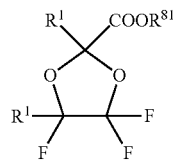

(8)

wherein $R^{81}$ is a group corresponding to the base, and $R^1$ are as defined above; and step E of heating the compound represented by formula (8) (in the present specification, also referred to as "compound (8)") to produce the compound represented by formula (5).

Compound (8) is a carboxylic acid salt of compound (6), corresponding to the above base.

$R^{81}$ is preferably an alkali metal atom, an alkaline earth metal atom, pyridinium, ammonium, or amino optionally substituted with an organic group; more preferably a potassium atom, a sodium atom, or ammonium; and particularly preferably a sodium atom or a potassium atom.

In the present specification, except for using the compound of formula (1) produced in step A or B as a raw material in step C, steps C, D, E, and F may be performed by a known method, for example, according to the method disclosed in JP2005-002014A, U.S. Pat. No. 3,308,107B, or U.S. Pat. No. 6,664,431B. These publications are incorporated herein by reference.

Step C

In step C, compound (1) produced in step A or B is isomerized by heating in the presence of compound (4) to produce compound (6).

In step C, compound (1) produced in step A or B may be used after isolation, or the liquid layer of the reaction liquid containing compound (1) obtained in step B may be used.

For the details of compound (4) in step C, the description of the details of compound (4) in step (A) is applied, unless otherwise specified.

The amount of compound (4) used in step C may be preferably within the range of 0.001 to 10 mol, more preferably 0.002 to 5.0 mol, and even more preferably 0.006 to 1.0 mol, per mol of compound (1).

Step C may be preferably performed in an organic solvent. Examples and preferred examples of organic solvents are the same as those mentioned above. Preferred specific examples of organic solvents include diethylene glycol dimethyl ether, triethylene glycol dimethyl ether, tetraethylene glycol dimethyl ether, 1,4-dicyanobutane, acetonitrile, 1,2-dimethylether, tetrahydrofuran, and dimethylsulfoxide.

The amount of the organic solvent used in step C may be an amount that can function as a solvent, based on common technical knowledge etc.

The reaction temperature in step C may be preferably within the range of 50 to 300° C., more preferably 50 to 200° C., and even more preferably 100 to 180° C.

The reaction time in step C may be preferably within the range of 0.5 hours to 60 hours, more preferably 1 hour to 24 hours, and even more preferably 2 hours to 24 hours.

Compound (6) produced in step C can be isolated or purified, if desired, by a conventional method, such as extraction, dissolution, concentration, precipitation, dehydration, adsorption, distillation, rectification, or chromatography, or a combination of these methods.

Step D

In step D, compound (6) is reacted with base (d) to produce compound (8). Compound (8) is a carboxylic acid salt of compound (6), corresponding to base (d).

Base (d) is, for example, at least one member selected from the group consisting of (1) acetate, carbonate, hydrogen carbonate, phosphate, hydrogen phosphate, alkoxide salts, hydroxide salts, hydride salts, ammonium salts, or amide salts of alkali or alkaline earth metals, (2) alkali metals, and (3) amines.

Examples of alkoxide salts include sodium methoxide, sodium ethoxide, sodium butoxide, potassium methoxide, potassium ethoxide, potassium butoxide, lithium methoxide, and lithium ethoxide.

Examples of hydroxide salts include sodium hydroxide, potassium hydroxide, lithium hydroxide, rubidium hydroxide, cesium hydroxide, magnesium hydroxide, calcium hydroxide, and barium hydroxide.

Examples of hydride salts include sodium hydride, potassium hydride, lithium hydride, and calcium hydride.

Examples of alkali metals include sodium, potassium, and lithium.

Examples of amines include aliphatic amines, alicyclic amines, aromatic amines, and heterocyclic amines. The amines may be preferably tertiary amines.

Base (d) is preferably at least one member selected from the group consisting of sodium methoxide, sodium hydroxide, potassium hydroxide, sodium carbonate, potassium carbonate, sodium hydrogen carbonate, potassium hydrogen carbonate, cesium carbonate, and ammonia.

Base (d) is more preferably at least one member selected from the group consisting of potassium hydroxide, potassium hydrogen carbonate, potassium carbonate, and sodium carbonate.

Step D may be preferably performed in an organic solvent. Examples and preferred examples of organic solvents are the same as those mentioned above. Preferred specific examples of organic solvents include methanol, ethanol, diethylene glycol dimethyl ether, triethylene glycol dimethyl ether, tetraethylene glycol dimethyl ether, 1,4-dicyanobutane, 1,2-dimethylether, tetrahydrofuran, and acetonitrile.

The amount of base (d) used in step D may be preferably within the range of 0.05 to 10 mol, more preferably 0.1 to 10 mol, and even more preferably 0.1 to 5 mol, per mol of compound (6).

The amount of the organic solvent used in step D may be an amount that can function as a solvent, based on common technical knowledge etc.

The reaction temperature in step D may be preferably within the range of −50 to 120° C., more preferably −20 to 100° C., and even more preferably −10 to 70° C.

The reaction time in step D may be preferably within the range of 0.1 hours to 24 hours, more preferably 0.1 hours to 12 hours, and even more preferably 0.1 hours to 6 hours.

Compound (8) produced in step D can be isolated or purified, if desired, by a conventional method, such as extraction, dissolution, concentration, precipitation, dehydration, adsorption, distillation, rectification, or chromatography, or a combination of these methods.

Step E

In step E, compound (8) is thermally decomposed by heating to produce compound (5). Compound (5) is useful as an intermediate etc. for the production of raw materials of resin materials.

Step E may be performed in an organic solvent or without a solvent. Examples and preferred examples of organic solvents are the same as those mentioned above. Preferred specific examples of organic solvent include ethyl acetate, butyl acetate, propyl acetate, methyl propionate, ethyl propionate, 1,2-dimethoxyethane, diethylene glycol dimethyl ether, triethylene glycol dimethyl ether, tetraethylene glycol dimethyl ether, 1,4-dicyanobutane, and acetonitrile.

The amount of the organic solvent used in step E may be an amount that can function as a solvent, based on common technical knowledge etc.

When a solvent is contained, the reaction temperature in step E may be preferably within the range of 100 to 400° C., more preferably 100 to 300° C., and even more preferably 100 to 200° C.

When a solvent is not contained, the reaction temperature in step E may be preferably within the range of 100 to 400° C., more preferably 150 to 400° C., and even more preferably 150 to 350° C.

The reaction time in step E may be preferably within the range of 0.1 hours to 24 hours, more preferably 0.1 hours to 12 hours, and even more preferably 0.1 hours to 6 hours.

The reaction in step E may be performed in the presence or absence of an inert gas (e.g., nitrogen gas), and preferably in the absence of an inert gas.

Step E can be performed under reduced pressure, atmospheric pressure, or increased pressure.

Compound (5) produced in step E can be isolated or purified, if desired, by a conventional method, such as extraction, dissolution, concentration, precipitation, dehydration, adsorption, distillation, rectification, or chromatography, or a combination of these methods.

An embodiment of the present disclosure is a method for producing the compound represented by formula (5), the method comprising, in place of step D:

step D1 of reacting the compound represented by formula (6) with water or alkyl alcohol to produce a compound represented by formula (7):

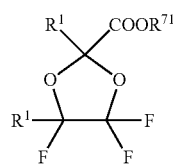

(7)

wherein $R^{71}$ is a hydrogen atom or an alkyl group, and $R^1$ are as defined above (in the present specification, also referred to as "compound (7)"); and step D2 of reacting the compound represented by formula (7) with a base (in the present specification, also referred to as "base (d2)") to produce the compound represented by formula (8).

$R^{71}$ is preferably a hydrogen atom or a linear or branched $C_{1-10}$ alkyl group, more preferably a hydrogen atom or a linear or branched $C_{1-5}$ alkyl group, even more preferably a linear or branched $C_{1-4}$ alkyl group, particularly preferably methyl, ethyl, n-propyl, isopropyl, n-butyl, sec-butyl, or tert-butyl, and further particularly preferably methyl or ethyl.

Step D1

In step D1, compound (6) is reacted with water or alkyl alcohol for conversion to a corresponding carboxylic acid or alkyl ester, thereby producing compound (7).

In step D1, compound (6) may be isolated, or the product liquid containing compound (6) produced in step C may be used as it is. The use of this product liquid is preferable because it is advantageous that the purification of compound (6) is not necessary.

The alkyl alcohol is preferably a linear or branched $C_0$ alkyl alcohol, more preferably a linear or branched $C_{1-5}$ alkyl alcohol, even more preferably a linear or branched $C_{1-4}$ alkyl alcohol, particularly preferably methanol, ethanol, n-propanol, isopropanol, n-butyl alcohol, sec-butyl alcohol, or tert-butyl alcohol, and further particularly preferably methanol or ethanol.

The amount of water, alkyl alcohol, or mixture of water and alcohol to be used in step D1 may be preferably within the range of 0.1 to 50 mol, more preferably 0.2 to 20 mol, and even more preferably 0.5 to 10 mol, per mol of compound (6).

In step D1, in addition to water and alkyl alcohol, other organic solvents may be further used. Examples and preferred examples of organic solvents are the same as those mentioned above. Specific examples of such organic solvents include 1,2-dimethoxyethane, diethylene glycol dimethyl ether, triethylene glycol dimethyl ether, tetraethylene glycol dimethyl ether, 1,4-dicyanobutane, and acetonitrile. The amount of the organic solvent can be preferably within the range of 0.01 to 50 mol, and more preferably 0.1 to 50 mol, per mol of compound (6).

The reaction temperature in step D1 may be preferably within the range of −50 to 50° C., more preferably −20 to 30° C., and even more preferably −20 to 20° C.

The reaction time in step D1 may be preferably within the range of 0.1 hours to 24 hours, more preferably 0.1 hours to 12 hours, and even more preferably 0.1 hours to 6 hours.

The reaction in step D1 may be performed in the presence or absence of an inert gas (e.g., nitrogen gas), and preferably in the absence of an inert gas.

Step D1 can be performed under reduced pressure, atmospheric pressure, or increased pressure.

Compound (7) produced in step D1 can be isolated or purified, if desired, by a conventional method, such as extraction, dissolution, concentration, precipitation, dehydration, adsorption, distillation, rectification, or chromatography, or a combination of these methods.

Compound (6) is reacted with alkyl alcohol to produce compound (7) in the reaction liquid, water is added to the reaction liquid, and the resulting organic layer is collected and distilled, whereby compound (7) can be easily purified, which is preferable.

Step D2

In step D2, compound (7) is reacted with base (d2) to produce compound (8). For the details of base (d2) in step D2, the description of the details of the base in step D is applied, unless otherwise specified.

The amount of base (d2) used in step D2 may be preferably within the range of 0.1 to 20 mol, more preferably 0.5 to 15 mol, and even more preferably 1 to 10 mol, per mol of compound (7).

Step D2 is preferably performed in the presence of an organic solvent. Examples and preferred examples of organic solvents are the same as those mentioned above.

The organic solvent is preferably methanol, ethanol, 1,2-dimethoxyethane, diethylene glycol dimethyl ether, triethylene glycol dimethyl ether, tetraethylene glycol dimethyl ether, 1,4-dicyanobutane, acetonitrile, or tetrahydrofuran. These organic solvents may be used singly or as a mixture of two or more.

The reaction temperature in step D2 may be preferably within the range of −50 to 120° C., more preferably −20 to 100° C., and even more preferably −10 to 70° C.

The reaction time in step D2 may be preferably within the range 0.1 hours to 24 hours, more preferably 0.1 hours to 12 hours, and even more preferably 0.1 hours to 6 hours.

The reaction in step D2 may be performed in the presence or absence of an inert gas (e.g., nitrogen gas), and preferably in the absence of an inert gas.

Step D2 can be performed under reduced pressure, atmospheric pressure, or increased pressure.

In step D2, compound (8) can precipitate as a solid in the solvent. When a solid precipitates, compound (8) can be easily isolated by removing the solvent. The solvent can be removed by any known method.

An embodiment of the present disclosure is a method for producing the compound represented by formula (5), the method further comprising step D1a of purifying the liquid produced in step D1 to obtain the compound represented by formula (7). The purified compound (7) may be subjected to step D2.

Step D1a

In step D1a, the reaction liquid produced in step D1 is purified to obtain compound (7). Compound (7) can be isolated or purified by a conventional method, such as extraction, dissolution, concentration, precipitation, dehydration, adsorption, distillation, rectification, or chromatography, or a combination of these methods. Preferably, the organic layer of the reaction liquid produced in step D1 is purified, more preferably by distillation, to easily obtain compound (7). The organic layer often contains no or only small amounts of other substances with a boiling point near the boiling point of compound (7), and is thus suitable for purification by distillation.

An embodiment of the present disclosure is a method for producing the compound represented by formula (5), the method comprising, in place of steps D and E, step F of heating the compound represented by formula (6) in the presence of a base (in the present specification, also referred to as "base (f)") to produce the compound represented by formula (5).

Step F

In step F, compound (6) is heated in the presence of base (f) to produce the compound represented by formula (5). Step F may be performed by a known method, for example, according to the method disclosed in U.S. Pat. No. 3,308,107B or U.S. Pat. No. 6,664,431B. These publications are incorporated herein by reference.

In step F, compound (6) may be isolated, or the product liquid containing compound (6) produced in step C may be used as it is. The use of this product liquid is preferable because it is advantageous that the purification of compound (6) is not necessary.

For the details of base (f) in step F, the description of the details of the base in step D is applied, unless otherwise specified.

Base (f) is preferably a hydroxide, halide, carbonate, or hydrogen carbonate of an alkali metal, or ammonia. The alkali metal halide may be carried on a carrier, such as activated carbon or inorganic oxide.

Base (f) is more preferably at least one member selected from the group consisting of sodium hydroxide, potassium hydroxide, sodium carbonate, potassium carbonate, cesium carbonate, sodium hydrogen carbonate, potassium hydrogen carbonate, ammonia, potassium fluoride, sodium fluoride, cesium fluoride, sodium chloride, and potassium iodide.

Base (f) is even more preferably at least one member selected from the group consisting of potassium hydroxide, potassium hydrogen carbonate, potassium carbonate, sodium carbonate, potassium fluoride, sodium fluoride, cesium fluoride, sodium chloride, and potassium iodide.

The carrier of base (f) is preferably activated carbon, an alkali metal oxide, an alkaline earth metal oxide, zinc oxide, aluminum oxide, nickel oxide, or silicon dioxide.

The carrier of base (f) is more preferably at least one member selected from the group consisting of alkaline earth metal oxides, aluminum oxide, and silicon dioxide.

Specific examples of alkali metal oxides include lithium oxide, sodium oxide, potassium oxide, rubidium oxide, and cesium oxide.

Specific examples of alkaline earth metal oxides include magnesium oxide, calcium oxide, and barium oxide.

Step F may be performed in an organic solvent or without a solvent. Examples and preferred examples of organic solvents are the same as those mentioned above. Preferred specific examples of organic solvents include ethyl acetate, propyl acetate, butyl acetate, methyl propionate, ethyl propionate, 1,2-dimethoxyethane, diethylene glycol dimethyl ether, triethylene glycol dimethyl ether, tetraethylene glycol dimethyl ether, 1,4-dicyanobutane, tetrahydrofuran, and acetonitrile.

The amount of base (f) used in step F may be preferably within the range of 0.1 to 200 mol, more preferably 0.5 to 100 mol, and even more preferably 1 to 50 mol, per mol of compound (6).

The amount of the inorganic oxide used in step F may be preferably within the range of 0.2 to 400 mol, more preferably 1 to 200 mol, and even more preferably 2 to 100 mol, per mol of compound (6).

The amount of the organic solvent used in step F may be an amount that can function as a solvent, based on common technical knowledge etc.

When a solvent is contained, the reaction temperature in step F may be preferably within the range of 80 to 400° C., more preferably 100 to 350° C., and even more preferably 100 to 300° C. When a solvent is not contained, the reaction temperature in step F may be preferably within the range of 100 to 400° C., more preferably 150 to 400° C., and even more preferably 150 to 350° C.

The reaction time in step F may be preferably within the range of 0.01 hours to 24 hours, more preferably 0.01 hours to 12 hours, and even more preferably 0.01 hours to 6 hours.

The reaction in step F may be performed in the presence or absence of an inert gas (e.g., nitrogen gas), and preferably in the absence of an inert gas.

Step F can be performed under reduced pressure, atmospheric pressure, or increased pressure.

Compound (5) produced in step F can be isolated or purified, if desired, by a conventional method, such as extraction, dissolution, concentration, precipitation, dehydration, adsorption, distillation, rectification, or chromatography, or a combination of these methods.

Compound

Among compounds that can be produced by the production method of the present disclosure, a compound represented by formula (7-1):

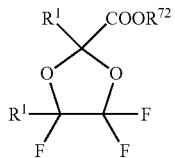

(7-1)

wherein two $R^1$ are the same and each is a fluorine atom or a fluoroalkyl group, and $R^{72}$ is an alkyl group (in the present specification, also referred to as "compound (7-1)"), is a novel compound. The present disclosure also provides such novel compounds. The novel compounds can be effectively used as raw materials, intermediates, or the like of monomers for the production of polymers.

In compound (7-1), $R^1$ are as described above.

In compound (7-1), $R^{72}$ is preferably a linear or branched $C_{1-10}$ alkyl group, more preferably a hydrogen atom or a linear or branched $C_{1-5}$ alkyl group, even more preferably a linear or branched $C_{1-4}$ alkyl group, particularly preferably methyl, ethyl, n-propyl, isopropyl, n-butyl, sec-butyl, or tert-butyl, and further particularly preferably methyl or ethyl.

In compound (7-1), preferably, $R^1$ are the same and each is a fluorine atom or a $C_{1-10}$ fluoroalkyl group, and $R^{72}$ is a linear or branched $C_{1-10}$ alkyl group.

In compound (7-1), more preferably, $R^1$ are the same and each is a fluorine atom or a $C_{1-5}$ perfluoroalkyl group, and $R^{72}$ is a linear or branched $C_{1-5}$ alkyl group.

In compound (7-1), even more preferably, $R^1$ are the same and each is a fluorine atom or a $C_{1-3}$ perfluoroalkyl group, and $R^{72}$ is a linear or branched $C_{1-4}$ alkyl group.

In compound (7-1), particularly preferably, $R^1$ are the same and each is a $C_{1-3}$ perfluoroalkyl group, and $R^{72}$ is methyl, ethyl, n-propyl, isopropyl, n-butyl, sec-butyl, or tert-butyl.

In compound (7-1), further particularly preferably, $R^1$ are the same and each is a $C_{1-3}$ perfluoroalkyl group, and $R^{72}$ is methyl or ethyl.

Method for Producing Compound Represented by Formula (7-1)

The present disclosure also provides a method for producing novel compound (7-1). This production method comprises step D1-1 of reacting the compound represented by formula (6) with alkyl alcohol to produce the compound represented by formula (7-1).

Compound (6) used in step D1-1 of the method for producing compound (7-1) may be the one produced in step C of the method for producing compound (5), or may be produced by a known technique. Other matters in this step are the same as those in step D1 of the method for producing compound (5), except that this step does not include reacting compound (6) with water.

Composition

An embodiment of the present disclosure is a composition comprising the compound represented by formula (5), and further comprising, based on 100 parts by mass of the compound represented by formula (5), 0.00001 to 1 part by mass of a compound represented by formula (9):

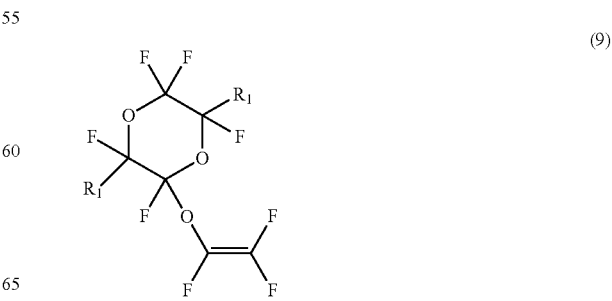

(9)

wherein two R¹ are as defined above (in the present specification, also referred to as "compound (9)"), and/or 0.00001 to 1 part by mass of a compound represented by formula (10):

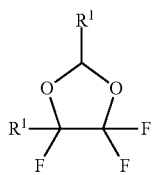
(10)

wherein two R¹ are as defined above (in the present specification, also referred to as "compound (10)").

The method for producing the compound represented by formula (5) of the present disclosure can also produce the composition described above. The composition may further contain compound (4-1), a polymerization inhibitor, water, or a polar solvent.

The amount of each of the components contained in the composition can be adjusted by setting the reaction conditions (e.g., temperature, time, type and amount of raw material, type and amount of solvent, and type and amount of catalyst). Further, the amounts of the various components can be adjusted by purification after the production of compound (5).

For the details of R¹ in the composition, the description of the details of R¹ in the method for producing the compound represented by formula (1) is applied, unless otherwise specified.

Preferred specific examples of compound (9) include 2,2,3,5,6-pentafluoro-3,6-bis(trifluoromethyl)-5-((1,2,2-trifluorovinyl)oxy)-1,4-dioxane.

The quantitative ratio of compound (9) in the composition is preferably 0.00001 to 1 part by mass, more preferably 0.00001 to 0.8 parts by mass, even more preferably 0.00001 to 0.5 parts by mass, and particularly preferably 0.0001 to 0.1 parts by mass, based on 100 parts by mass of compound (5).

Preferred specific examples of compound (10) include perfluoro-2,4-dimethyl-1,3-dioxolane.

The quantitative ratio of compound (10) in the composition is preferably 0.00001 to 1 part by mass, more preferably 0.00001 to 0.8 parts by mass, even more preferably 0.00001 to 0.5 parts by mass, and particularly preferably 0.0001 to 0.1 parts by mass, based on 100 parts by mass of compound (5).

The composition may contain either or both of compounds (9) and (10). The composition preferably contains 0.00001 to 0.8 parts by mass of compound (9) and/or 0.00001 to 0.8 parts by mass of compound (10), more preferably 0.00001 to 0.5 parts by mass of compound (9) and/or 0.00001 to 0.5 parts by mass of compound (10), and particularly preferably 0.0001 to 0.1 parts by mass of compound (9) and/or 0.0001 to 0.1 parts by mass of compound (10), based on 100 parts by mass of compound (5).

Preferred specific examples of compound (4-1) and the symbols in formula (4-1) are the same as those of compound (4-1) in the method for producing the compound represented by formula (1).

Preferred specific examples of polar solvents include alcohol solvents, ether solvents, ester solvents, and nitrile solvents.

Preferred specific examples of alcohol solvents include methanol, ethanol, isopropanol, and tert-butyl alcohol.

Preferred specific examples of ester solvents include methyl formate, ethyl formate, methyl acetate, ethyl acetate, isopropyl acetate, methyl propionate, ethyl propionate, and n-butyl acetate.

Preferred specific examples of nitrile solvents include 1,4-dicyanobutane, acetonitrile, and benzonitrile.

Preferred specific examples of ether solvents include diethylene glycol dimethyl ether, triethylene glycol dimethyl ether, tetraethylene glycol dimethyl ether, diethyl ether, diisopropyl ether, dioxane, tetrahydrofuran, and 1,2-dimethoxyethane.

Preferred specific examples of polar solvents include methanol, ethanol, isopropanol, tert-butyl alcohol, diethylene glycol dimethyl ether, triethylene glycol dimethyl ether, tetraethylene glycol dimethyl ether, 1,4-dicyanobutane, acetonitrile, and tetrahydrofuran.

Preferred examples of polymerization inhibitors include 4-methoxy-1-naphthol, hydroquinone, hydroquinone methyl ether, dimethyl-t-butylphenol, 2,6-di-tert-butyl-p-cresol, and benzotriazole.

The quantitative ratio of compound (4-1) in the composition is preferably 0.00001 to 0.1 parts by mass, more preferably 0.00001 to 0.08 parts by mass, even more preferably 0.00001 to 0.05 parts by mass, and particularly preferably 0.00001 to 0.01 parts by mass, based on 100 parts by mass of compound (5).

The quantitative ratio of the polar solvent in the composition is preferably 0.00001 to 0.1 parts by mass, more preferably 0.00001 to 0.08 parts by mass, even more preferably 0.00001 to 0.05 parts by mass, and particularly preferably 0.0001 to 0.01 parts by mass, based on 100 parts by mass of compound (5).

The quantitative ratio of the polymerization inhibitor in the composition is preferably 0.00001 to 1 part by mass, more preferably 0.00001 to 0.8 parts by mass, even more preferably 0.00001 to 0.5 parts by mass, and particularly preferably 0.00001 to 0.1 parts by mass, based on 100 parts by mass of compound (5).

The quantitative ratio of water in the composition is preferably 0.00001 to 0.1 parts by mass, more preferably 0.00001 to 0.08 parts by mass, even more preferably 0.00001 to 0.05 parts by mass, and particularly preferably 0.00001 to 0.01 parts by mass, based on 100 parts by mass of compound (5).

Within the range of the above quantitative ratios, the composition of the present disclosure can be suitably used, for example, as a raw material for resin materials. In addition, it is advantageous in terms of the production costs of the composition, and thereby also advantageous in terms of the production costs of the final product.

Although the embodiments are described above, it will be understood that various changes in form and details can be made without departing from the spirit and scope of the claims.

The present disclosure includes, for example, the following embodiments.

Item 1.

A method for producing a compound represented by formula (1):

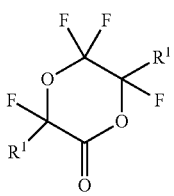
(1)

wherein two $R^1$ are the same and each is a fluorine atom or a fluoroalkyl group,
the method comprising step A of reacting a compound represented by formula (2):

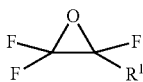
(2)

wherein $R^1$ is as defined above, with at least one compound (3) selected from the group consisting of:
a compound represented by formula (3-1):

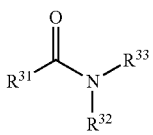
(3-1)

wherein $R^{31}$, $R^{32}$, and $R^{33}$ are the same or different and each is a hydrogen atom or a $C_{1-10}$ alkyl group, or two of them are optionally linked to each other to form a ring optionally having one or more substituents; and
a compound represented by formula (3-2):

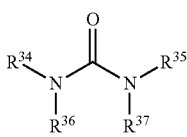
(3-2)

wherein $R^{34}$, $R^{35}$, $R^{36}$, and $R^{37}$ are the same or different and each is a hydrogen atom or a $C_{1-10}$ alkyl group, or two of them are optionally linked to each other to form a ring optionally having one or more substituents,
in the presence of at least one fluorine compound (4) selected from the group consisting of:
a compound represented by formula (4-1):

$MH_nF_m$ (4-1)

wherein M is a metal atom, n is 0 or 1, and the sum of the valence number of M and n is m;
a compound represented by formula (4-2):

$LR^{41}_4F$ (4-2)

wherein L is a nitrogen atom or a phosphorus atom, and $R^{41}$ are the same or different and each is a $C_{1-5}$ alkyl group; and
hydrofluoric acid or a salt thereof, and an organic solvent, provided that the compounds represented by formulas (3-1) and (3-2) are excluded from the organic solvent.

Item 2.
The production method according to Item 1, wherein two $R^1$ are the same and each is a $C_{1-10}$ fluoroalkyl group.
Item 3.
The production method according to Item 1 or 2, wherein step A is a step of generating an upper liquid layer and a lower liquid layer, and the method further comprises step B of performing liquid separation.
Item 4.
A method for producing a compound represented by formula (5):

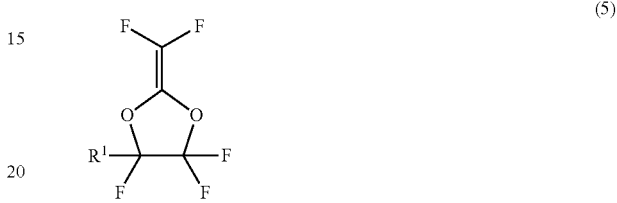
(5)

wherein $R^1$ is a fluorine atom or a fluoroalkyl group, the method comprising:
step C of heating a compound represented by formula (1) produced in step A or B:

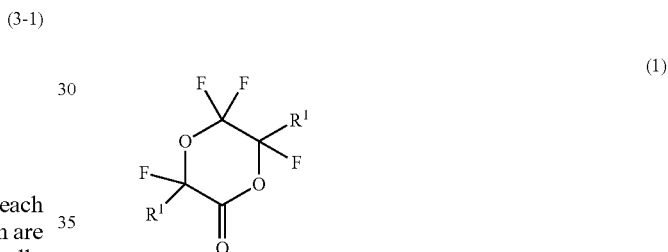
(1)

wherein two $R^1$ are the same and each is a fluorine atom or a fluoroalkyl group, in the presence of at least one fluorine compound (4) selected from the group consisting of:
a compound represented by formula (4-1):

$MH_nF_m$ (4-1)

wherein M is a metal atom, n is 0 or 1, and the sum of the valence number of M and n is m;
a compound represented by formula (4-2):

$LR^{41}_4F$ (4-2)

wherein L is a nitrogen atom or a phosphorus atom, and $R^{41}$ are the same or different and each is a $C_{1-5}$ alkyl group; and
hydrofluoric acid or a salt thereof, to produce a compound represented by formula (6):

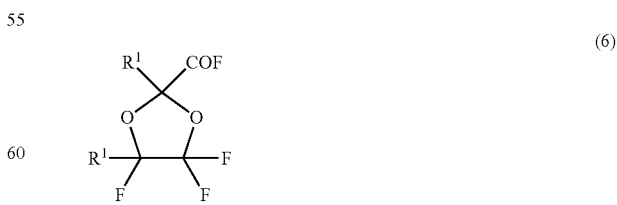
(6)

wherein $R^1$ are as defined above;
step D of reacting the compound represented by formula (6) with a base to produce a compound represented by formula (8):

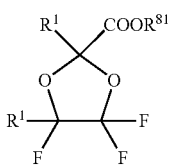

(8)

wherein $R^{81}$ is a group corresponding to the base, and $R^1$ are as defined above; and step E of heating the compound represented by formula (8) to produce the compound represented by formula (5).

Item 5.

The method according to Item 4, comprising, in place of step D:

step D1 of reacting the compound represented by formula (6) with water or alkyl alcohol to produce a compound represented by formula (7):

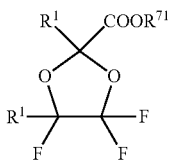

(7)

wherein $R^{71}$ is a hydrogen atom or an alkyl group, and $R^1$ are as defined above; and step D2 of reacting the compound represented by formula (7) with a base to produce the compound represented by formula (8).

Item 6.

The production method according to Item 5, further comprising step D1a of purifying a liquid produced in step D1 to obtain the compound represented by formula (7).

Item 7.

The method according to Item 4, comprising, in place of steps D and E, step F of heating the compound represented by formula (6) in the presence of a base to produce the compound represented by formula (5).

Item 8.

A compound represented by formula (7-1):

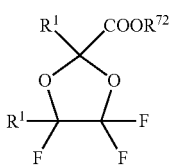

(7-1)

wherein two $R^1$ are the same and each is a fluorine atom or a fluoroalkyl group, and $R^{72}$ is an alkyl group.

Item 9.

The compound according to Item 8, wherein $R^{72}$ is a linear or branched $C_{1-10}$ alkyl group.

Item 10.

The compound according to Item 8, wherein $R^{72}$ is methyl, ethyl, n-propyl, isopropyl, n-butyl, sec-butyl, or tert-butyl.

Item 11.

A method for producing the compound according to Item 8, comprising step D1-1 of reacting a compound represented by formula (6):

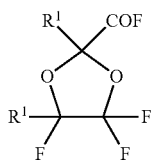

(6)

wherein two $R^1$ are the same and each is a fluorine atom or a fluoroalkyl group, with alkyl alcohol to produce a compound represented by formula (7-1):

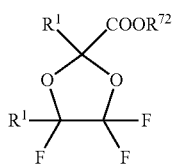

(7-1)

wherein $R^{72}$ is an alkyl group, and $R^1$ are as defined above.

Item 12.

A composition comprising a compound represented by formula (5):

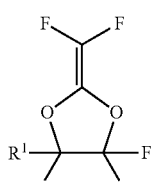

(5)

wherein $R^1$ is a fluorine atom or a fluoroalkyl group, and further comprising, based on 100 parts by mass of the compound represented by formula (5), 0.00001 to 1 part by mass of a compound represented by formula (9):

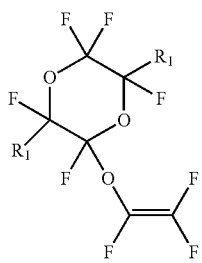

(9)

wherein two $R^1$ are as defined above, and/or 0.00001 to 1 part by mass of a compound represented by formula (10):

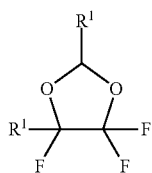
(10)

wherein two R¹ are as defined above.

Item 13.

The composition according to Item 12, wherein the compound represented by formula (9) is contained in an amount of 0.00001 to 0.5 parts by mass, and/or the compound represented by formula (10) is contained in an amount of 0.00001 to 0.5 parts by mass, based on 100 parts by mass of the compound represented by formula (5).

EXAMPLES

An embodiment of the present disclosure is described in more detail below with Examples; however, the present disclosure is not limited thereto.

The symbols and abbreviations in the Examples are used with the following meanings.

CsF: cesium fluoride
GC: gas chromatography
DMF: N, N-dimethylformamide
diglyme: diethylene glycol dimethyl ether
Me: methyl Compound 1a: a compound represented by the following formula (1a):

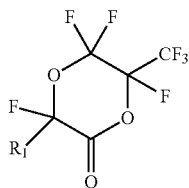
(1a)

Compound 6a: a compound represented by the following formula (6a):

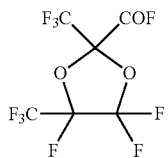
(6a)

Compound 8a: a compound represented by the following formula (8a):

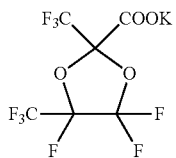
(8a)

Compound 5a: a compound represented by the following formula (5a):

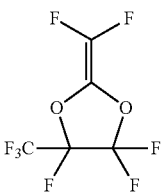
(5a)

Compound 9a: a compound represented by the following formula (9a):

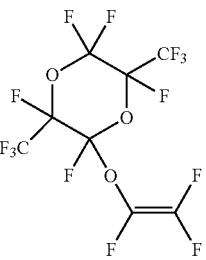
(9a)

Compound 10a: a compound represented by the following formula (10a):

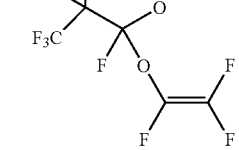
(10a)

Compound 11a: a compound represented by the following formula (11a):

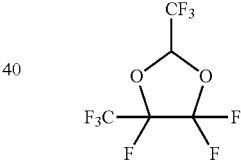
(11a)

Compound 11b: a compound represented by the following formula (11b):

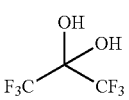
(11b)

Compound 12a: a compound represented by the following formula (12a):

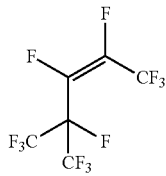

(12a)

Compound 13a: a compound represented by the following formula (13a):

$CF_2=CFOCF_2CF_2CF_3$ (13a)

Compound 7a: a compound represented by the following formula (7a):

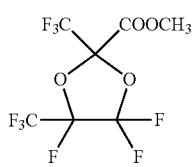

(7a)

Compound 14a: a compound represented by the following formula (14a):

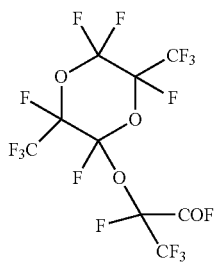

(14a)

Compound 14b: a compound represented by the following formula (14b):

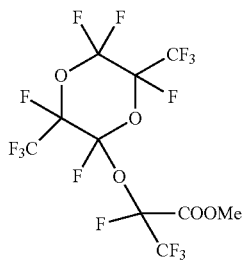

(14b)

Compound 14c: a compound represented by the following formula (14c):

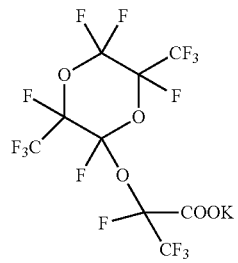

(14c)

Compound 15a: a compound represented by the following formula (15a):

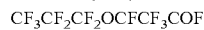

$CF_3CF_2CF_2OCFCF_3COF$ (15a)

Compound 15b: a compound represented by the following formula (15b):

$CF_3CF_2CF_2OCFCF_3COOMe$ (15b)

Compound 15c: a compound represented by the following formula (15c):

$CF_3CF_2CF_2OCFCF_3COOK$ (15c)

Compound 16a: a compound represented by the following formula (16a):

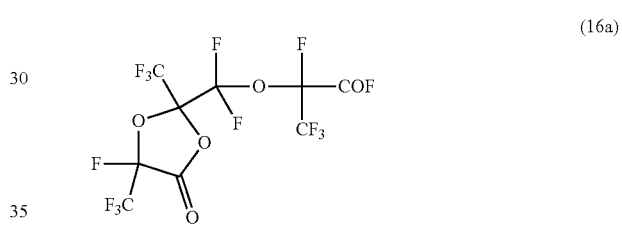

(16a)

Example 1: Steps A and B 0.83 g of CsF (2.5 mmol), 9.03 g of DMF (0.12 mol), and 16.6 g of diglyme (0.12 mol) were added to a reactor and cooled to −20° C. 44 g of propylene oxide hexafluoride (0.27 mol) was added to the reactor, and the mixture was stirred for 2 hours. After the propylene oxide hexafluoride disappeared, the reaction liquid was collected. The reaction liquid was separated in two layers: an upper layer liquid and a lower layer liquid. The reaction liquid was separated, and 29 g of the upper layer liquid and 40 g of the lower layer liquid were each collected. The upper layer liquid and the lower layer liquid were analyzed by GC. Compound 1a at 63 GC % was obtained with a yield of 52%. Compound 1a: 63 GC %, hexafluoropropylene: 10 GC %, compound 14a: 15 GC % or less, compound 11a (H): 0.1 GC %, CsF: 0.1% or less, compound 15a: 1.0 GC %, $(CH_3)_2NCF_2H$: 0.5 GC %, compound 16a: 6.0 GC %, diglyme: 1.0 GC % or less "% or less" means that the content of various components is 0.0000095% or more and within the range of percentage or less of the specifically described value. The same applies to the following examples.

The CsF content was measured by the NMR method.

The contents of the other components were measured by the GC method.

Comparative Example 1: Synthesis of Compound 1a in Two Steps 4.27 g of DMF (0.06 mol) was added to a reactor and cooled to −27° C. 12 g of propylene oxide hexafluoride (0.07 mol) was added to the reactor, and the mixture was stirred for 1 hour. After stirring, the reaction liquid was collected. The reaction liquid was analyzed by NMR. 4-Fluoro-5-oxo-2,4-bis(trifluoromethyl)-1,3-dioxolane-2-carbonyl fluoride, which was a precursor of the target product, was obtained with a yield of 5%. Due to the very low yield of the precursor, the second step was not performed.

Example 2: Step C 20 g of a lower layer liquid (containing 13 g of compound 1a) obtained in the same manner as in Example 1, 3.2 g of CsF (21 mmol), and 7.1 g of diglyme (53 mmol) were added to a reactor, and heated to 120° C. for 12 hours to obtain a reaction liquid. In the reaction liquid, the upper layer liquid and the lower layer liquid were analyzed by GC. 7.2 g of compound 6a was obtained at a purity of 74%.

Compound 6a: 74 GC %, hexafluoropropylene: 2.0 GC %, compound 1a: 1.1 GC %, compound 14a: 3.0 GC % or less, compound 11a (H): 0.1 GC %, CsF: 0.1% or less, compound 15a: 0.1 GC %, $(CH_3)_2NCF_2H$: 0.1 GC % or less, diglyme: 15 GC % or less The CsF content was measured by the NMR method.

The contents of the other components were measured by the GC method.

Example 3: Step D

The lower layer liquid containing 7.2 g of compound 6a obtained in Example 2 was added to 12.7 g of potassium carbonate (0.09 mol) and 28 g of dimethoxyethane (0.3 mol), and the mixture was stirred at 60° C. for 2 hours to obtain a reaction liquid. The reaction liquid was filtered to obtain a filtrate, and the filtrate was concentrated. As a result of NMR analysis, a concentrate containing 7.0 g of compound 8a was obtained (yield: 44%).

Compound 8a: 80%, compound 14c: 3.0% or less, compound 11a (H): 0.1%, CsF: 1.0% or less, KF: 1.0% or less, compound 15c: 0.1%, water: 0.1% or less, diglyme: 10% or less The water content was measured by Karl Fischer electrometric titration method.

The contents of the other components were measured by the NMR method.

Example 4: Step E 6.7 g of compound 8a obtained in Example 3 was added to a reactor, and heated at 200° C. for 4 hours and at 300° C. for 1 hour. The resulting product was collected in a trap at −78° C. and analyzed by NMR and GC. As a result, compound 5a was obtained with a yield of 60% and at a purity of 95%.

Compound 5a: 95 GC %, hexafluoropropylene: 0.01 GC %, compound 9a: 1.0 GC % or less, compound 11a (H): 0.1 GC %, compound 11b (Me): 0.1 GC %, compound 12a: 0.1 GC %, CsF: 0.1% or less, KF: 0.1% or less, compound 13a: 0.1 GC %, compound 10a: 0.2 GC % or less, diglyme: 4.0 GC % or less, water: 0.1% or less The contents of CsF and KF were measured by an ion chromatography method. In the ion chromatography method, a liquid obtained by liquid-liquid extraction of a sample with the same volume of ultrapure water as a pretreatment was used for the measurement.

The water content was measured by Karl Fischer electrometric titration method.

The contents of the other components were measured by the GC method.

Example 5: Step D1

32 g (1 mol) of methanol and 45 g of water were added to 83 g of an upper layer liquid and 79 g of a lower layer liquid obtained in the same manner as in Example 2, and the mixture was stirred for 2 hours. The product liquid was separated in two layers, and the lower layer liquid was collected by liquid separation and distilled (150° C., 5 hours), thereby obtaining compound 7a. The yield was 47%. −77 ppm (1F, CF2), −81 ppm (3F, CFCF3), −82 ppm (3F, CF3), −83 ppm (1F, CF2), −124 ppm (1F, CFCF3)

Compound 7a: 98 GC %, compound 14b: 0.1 GC % or less, compound 11a (H): 0.1 GC %, compound 11b (Me): 0.1 GC %, compound 15b: 0.1 GC %, water: 0.1% or less The water content was measured by Karl Fischer electrometric titration method.

The contents of the other components were measured by the GC method.

Example 6: Step D2

0.13 mol of potassium hydroxide was added to 42 g of methanol. The methanol solution was added to a glass reactor. 0.13 mol of compound 7a was gradually added to the methanol solution, and the mixture was stirred at 20° C. for 1 hour. The solvent was removed from the reaction liquid in a concentrator, and the resulting solid was collected. This solid was dried under reduced pressure to obtain a stoichiometric amount of compound 8a.

The invention claimed is:

1. A composition comprising a compound represented by formula (5):

(5)

wherein $R^1$ is a fluorine atom or a fluoroalkyl group, and 0.00001 to 0.1 parts by mass of CsF based on 100 parts by mass of the compound represented by formula (5), and further comprising, based on 100 parts by mass of the compound represented by formula (5), 0.00001 to 1 part by mass of a compound represented by formula (9):

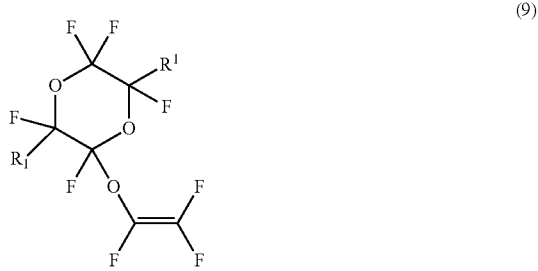

(9)

wherein two $R^1$ are as defined above, and/or 0.00001 to 1 part by mass of a compound represented by formula (10):

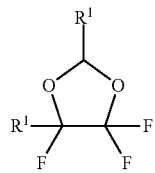

(10)

wherein two $R^1$ are as defined above.

2. The composition according to claim 1, wherein the compound represented by formula (9) is contained in an amount of 0.00001 to 0.5 parts by mass, and/or the compound represented by formula (10) is contained in an amount of 0.00001 to 0.5 parts by mass, based on 100 parts by mass of the compound represented by formula (5).

* * * * *